United States Patent [19]

Shibanai

[11] Patent Number: 4,725,633

[45] Date of Patent: Feb. 16, 1988

[54] PROCESS FOR THE PREPARATION OF ODORED SYNTHETIC LEATHER

[76] Inventor: Ichiro Shibanai, 10-6-312, Akasaka 6-chome, Minato-ku, Tokyo, Japan

[21] Appl. No.: 815,339

[22] Filed: Dec. 31, 1985

[51] Int. Cl.$^4$ .............................................. A61K 7/46
[52] U.S. Cl. ................................... 523/220; 428/904; 428/905; 106/155; 524/47; 524/56; 524/58; 512/4; 527/300; 527/313
[58] Field of Search ............... 523/220; 428/904, 905; 106/155; 524/47, 56, 58; 252/522 A, 522 R; 527/300, 313

[56] References Cited

U.S. PATENT DOCUMENTS

| | | | |
|---|---|---|---|
| 4,287,252 | 9/1981 | Dimiter | 428/904 |
| 4,303,787 | 12/1981 | Horikoshi et al. | 536/103 |
| 4,356,115 | 10/1982 | Shibanai et al. | 252/522 A |

Primary Examiner—Morton Foelak
Assistant Examiner—M. L. Moore
Attorney, Agent, or Firm—Jordan and Hamburg

[57] ABSTRACT

The present invention relates to a process for the preparation of a synthetic leather which comprises converting a leather perfume into the corresponding cyclodextrin clathrate compound, powdering the clathrate compound by drying, mixing the powder with a synthetic resin material and molding the mixture to form a synthetic leather material, thus imparting a natural leather-like material odor to the synthetic leather.

12 Claims, No Drawings

PROCESS FOR THE PREPARATION OF ODORED SYNTHETIC LEATHER

BACKGROUND OF THE INVENTION

1. Field of the Invention

The present invention relates to a process for the preparation of an odored synthetic leather which comprises adding a leather perfume to a synthetic resin raw material for the preparation of a synthetic leather to thereby impart a natural leather-like odor to the raw material.

2. Description of the Prior Art

Recently, an advancement in the technique for the preparation of a synthetic leather has made it possible to obtain a synthetic leather which is almost equivalent to a natural leather in appearance and touch. However, from the standpoint of odor, it is difficult to mold a synthetic resin containing a perfume into an odored product, so that no synthetic leather having a satisfactory natural leather-like odor has been prepared as yet.

The inventors of the present invention have established an invention entitled "Synthetic resin article having a scent and process for the preparation thereof" (Japanese Patent Publication No. 50058/1980) and succeeded in the preparation of a synthetic resin having a scent.

SUMMARY OF THE INVENTION

The present invention provides a process for the preparation of a synthetic leather having a natural leather-like odor, which comprises converting a leather perfume into the corresponding clathrate compound with cyclodextrin or a cyclo- dextrin-containing decomposed starch, powdering the clathrate compound by drying, mixing the powder with a synthetic resin material and, if necessary, further together with a polar solvent, and molding the resulting mixture.

DETAILED DESCRIPTION OF PREFERRED EMBODIMENTS

When a urethane resin material, vinyl acetate resin material or the like is used as the synthetic resin material, a polar solvent must be used, because such resin material is difficult to mix with a cyclodextrin clathrate compound of a leather perfume. Examples of the polar solvent include dimethylformamide, N-methyl-2-pyrrolidone, dimethylaminoacetate, dimethylacetamide, acetonitrile and the like.

When the resin material contains a plasticizer or a solvent, a powder of cyclodextrin clathrate compound of a leather perfume may be dispersed in such a plasticizer, solvent or the like, followed by the kneading or mixing of the resulting dispersion with a resin material. The plasticizer to be used is varied depending upon the kind of a resin and may be one selected from among phthalate, phosphate, fatty acid ester, adipate, epoxy (for example, methyl epoxystearate or epoxy soyabean oil), polyhydric alcohol ester plasticizers and the like. Examples of the solvent for polyester or polyurethane include diethylene glycol and triethylene glycol and those for fluoroplastics include chloroform, while those for guanamine resin or phenolic resin include formalin. Additionally, ethyl glycol, ethyl diglycol or the like can be used as the solvent.

The cyclodextrin to be used in the present invention is a specific dextrin having a structure where D-glucose molecules are bonded by an α-1,4 linkage to form a ring and is characterized by having a doughnut-like molecular structure having a cavity of a diameter of 6 to 10 Å therein. There are three types, i.e. α-, β- and γ-types of cyclodextrin depending upon the number of D-glucose units and any type of cyclodextrin can be used in the present invention. Among these types, β-cyclodextrin is a white crystalline powder and represented by the molecular formula $(C_6H_{10}O_5)_7$ and has a molecular weight of 1135 and a melting point of 300° to 305° C. (dec.).

The cyclodextrin-containing decomposed starch to be used in the present invention instead of cyclodextrin can be prepared by various methods. For example, it can be obtained as an intermediate product in preparing cyclodextrin by the action of cyclodextrin-generating enzyme produced by a microorganism of the genus Bacillus on starch. The process will now be described in more detail.

A starch solution is adjusted to a pH of 10, homogeneously gelatinized and cooled. Cyclodextrin glycosyltransferase, which is a fermentation product of a microorganism selected from among Bacillus Nos. 13, 17-1, 38-2, 135 and 169 bacteria, has an optimum pH in an alkaline region and exhibits a high temperature stability, is added to the solution to carry out the reaction. The reaction mixture is heated to deactivate the enzyme and cooled, followed by adjusting the pH to 5.0. A commercially available glucamylase is added to the reaction mixture to decompose unreacted substances. The resulting reaction mixture is filtered by an ordinary method and concentrated to give a cyclodextrin concentration of about 40% or above. A small amount of cyclodextrin is added to the concentrated reaction mixture as a seed. The resulting mixture is allowed to stand, thus precipitating cyclodextrin. The precipitated cyclodextrin is filtered off and dried to obtain β-cyclodextrin, while the objective cyclodextrin-containing decomposed starch is obtained as the resulting filtrate (see Japanese Patent Publication No. 43897/1977).

The above-described Bacillus Nos. 13, 17-1, 38-2, 135 and 169 bacteria have been deposited with the Fermentation Research Institute of the Agency of Industrial Science and Technology under FERM Nos. 611, 612, 614, 617 and 618, respectively.

A condensate obtained by purifying the above described filtrate with an ion exchange resin and condensing the purified filtrate is generally put on the market as a cyclodextrin-containing malt syrup. This cyclodextrin-containing malt syrup can be also used in the present invention.

The cyclodextrin-containing decomposed starch to be used in the present invention is not restricted to ones prepared by the above method, but may be any decomposed starch containing α, β- or γ- cyclodextrin or a mixture thereof which has been prepared by any method.

Examples of the leather perfume to be used in the present invention include one comprising thymol, labdanum, thyme oil, patchouli oil, eugenol, benzyl acetate and isobutylquinoline and one comprising methylionone, isoamylsalicylate, thymol eugenol, nutmeg oil and benzyl benzoate.

The clathrate compound of a leather perfume with cyclodextrin can be prepared by various methods including, for example, kneading. That is, about 0.1 to 6 times by weight as much water or hot water as cyclodextrin is added to cyclodextrin to obtain a paste or a suspension. About 0.1 to 3 times by weight as much of a leather perfume as the cyclodextrin is added to the paste or suspension. The resulting mixture is sufficiently kneaded by a ball mill, dispermill or the like. The kneading time is 0.5 to 12 hours, preferably 1 to 3 hours. When cyclodextrin is added to a leather perfume and the mixture is kneaded sufficiently as described above, the leather perfume enters into a cavity within a cyclodextrin molecule to form the corresponding clathrate compound. The resulting paste after the formation of the clathrate compound is dried and powdered with a vacuum dryer or a spray dryer. The formation of the clathrate compound and the powdering are preferably carried out at 60° C. or below.

Examples of the synthetic resin to be used in the present invention include vinyl chloride resin, vinyl acetate resin, polyurethane, polyester, guanamine resin, phenolic resin and fluoroplastics.

Now, the following Examples will further describe the process for the preparation of an odored synthetic leather according to the present invention.

EXAMPLE 1

85 parts by weight of α-cyclodextrin was added to 15 parts by weight of a leather perfume (thymol, labdanum, thyme oil, patchouli oil, eugenol, benzyl acetate or isobutylquinoline). The mixture was stirred for one hour, while keeping it at 50° C. to obtain a cyclodextrin clathrate compound of the leather perfume. The clathrate compound was powdered at a drying temperature of 60° C. with a vacuum dryer or a spray dryer into a particle size smaller than 150 mesh. 10 parts by weight of the resulting powder was mixed with 90 parts by weight of a non-rigid vinyl chloride resin compound. The mixture was molded by high expansion molding to obtain a synthetic leather automobile door trim having a leather odor.

EXAMPLE 2

85 parts by weight of α-cyclodextrin was added to 15 parts by weight of a leather perfume (methylionone, isoamyl salicylate, thymol eugenol, nutmeg oil or benzyl benzoate). The mixture was stirred for one hour, while keeping it at 50° C. to obtain a cyclodextrin clathrate compound of the leather perfume. The clathrate compound was powdered at a drying temperature of 60° C. with a vacuum dryer or a spray dryer into a particle size smaller than 150 mesh. The resulting powder was dispersed in dimethylformamide. The resulting dispersion was mixed with a urethane resin material comprising polyisocyanate, polyol, blowing agent, catalyst and stabilizer. The mixture was molded by slab expansion molding to obtain a synthetic leather for an automobile seat.

As described above, according to the present invention, a synthetic leather having a natural leather-like odor can be prepared and the odor can be maintained for a long period. Accordingly, when such a synthetic leather is used as an automobile interior trim, the gorgeousness can be felt sensually as well as visually.

What is claimed is:

1. A process for the preparation of an odored synthetic leather comprising converting a leather perfume into a corresponding clathrate compound with cyclodextrin or a cyclodextrin-containing decomposed starch, powdering the clathrate compound by drying, mixing the resulting powder with a synthetic resin material and a polar solvent to facilitate the mixing and molding the mixture to form an odored synthetic leather.

2. A process for the preparation of an odored synthetic leather comprising converting a leather perfume selected from the group consisting of thymol, labdanum, thyme oil, patchouli oil, eugenol, benzyl acetate and isobutylquinoline into a corresponding clathrate compound with cylodextrin or a cyclodextrin-containing decomposed starch, powdering the clathrate compound by drying, mixing the resulting power with a synthetic resin material and a polar solvent to facilitate the mixing and molding the mixture to form an odored synthetic leather.

3. A process as in claim 2, wherein the polar solvent is selected from the group consisting of dimethylformamide, N-methyl-2-pyrrolidone, dimethylaminoacetate, dimethylacetamide and acetonitrile.

4. A process as in claim 2, wherein the synthetic resin material is urethane or vinyl acetate resin material.

5. A process for the preparation of an odored synthetic leather comprising converting a leather perfume selected from the group consisting of methylionone, isoamylsalicylate, thymol eugenol, nutmeg oil and benzyl benzoate into a corresponding clathrate compound with cyclodextrin or a cyclodextrin-containing decomposed starch, powdering the clathrate compound by drying, mixing the resulting powder with a synthetic resin material and a polar solvent to facilitate the mixing and molding the mixture to form an odored synthetic leather.

6. A process as in claim 5, wherein the polar solvent is selected from the group consisting of dimethylformamide, N-methyl-2-pyrrolidone, dimethylaminoacetate, dimethylacetamide and acetonitrile.

7. A process as in claim 5, wherein the synthetic resin material is urethane or vinyl acetate resin material.

8. A process as in claim 1, wherein the polar solvent is selected from the group consisting of dimethylformamide, N-methyl-2-pyrrolidone, dimethylaminoacetate, dimethylacetamide and acetonitrile.

9. A process as in claim 1, wherein the synthetic resin material is urethane or vinyl acetate resin material.

10. A process as in claim 1, wherein the leather perfume is converted into the corresponding clathrate compound by kneading with cyclodextrin or a cyclodextrin-containing decomposed starch.

11. A process as in claim 2, wherein the leather perfume is converted into the corresponding clathrate compound by kneading with cyclodextrin or a cyclodextrin-containing decomposed starch.

12. A process as in claim 5, wherein the leather perfume is converted into the corresponding clathrate compound by kneading with cyclodextrin or a cyclodextrin-containing decomposed starch.

* * * * *